(12) United States Patent
Rose

(10) Patent No.: US 8,521,301 B2
(45) Date of Patent: Aug. 27, 2013

(54) THERMAL TREATMENT SYSTEM UTILIZING CONSTRUCTIVELY INTERFERING ELECTROMAGNETIC RADIATION

(75) Inventor: Gregory G. Rose, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 657 days.

(21) Appl. No.: 12/482,144

(22) Filed: Jun. 10, 2009

(65) Prior Publication Data
US 2010/0318162 A1   Dec. 16, 2010

(51) Int. Cl.
*A61N 1/40* (2006.01)
*A61N 7/02* (2006.01)

(52) U.S. Cl.
USPC ............................ 607/100; 607/101; 600/439

(58) Field of Classification Search
USPC .................................... 607/101, 100; 600/10
See application file for complete search history.

(56) References Cited

U.S. PATENT DOCUMENTS

| | | | | |
|---|---|---|---|---|
| 4,397,313 A | * | 8/1983 | Vaguine | 607/104 |
| 4,589,423 A | | 5/1986 | Turner | |
| 4,875,487 A | * | 10/1989 | Seppi | 600/439 |
| 5,540,737 A | * | 7/1996 | Fenn | 607/101 |
| 5,704,355 A | * | 1/1998 | Bridges | 600/407 |
| 5,713,946 A | | 2/1998 | Ben-Haim | |
| 5,723,001 A | | 3/1998 | Pilla et al. | |
| 6,112,110 A | * | 8/2000 | Wilk | 600/407 |
| 6,894,506 B2 | * | 5/2005 | Mohan et al. | 324/637 |
| 8,344,943 B2 | * | 1/2013 | Brown et al. | 342/147 |

OTHER PUBLICATIONS

International Search Report and Written Opinion—PCT/US2010/038204—International Search Authority, European Patent Office,Feb. 4, 2011.

* cited by examiner

*Primary Examiner* — Linda Dvorak
*Assistant Examiner* — Jared W Pike
(74) *Attorney, Agent, or Firm* — James T. Hagler

(57) ABSTRACT

Methods and systems enable thermal treating a portion of a subject using microwave or other electromagnetic radiation without harming other portions of the subject. In an embodiment, a plurality of electromagnetic radiation transmitters are positioned within a thermal treatment system and coupled to a control processor. The electromagnetic radiation may be transmitted as a pseudorandom waveform and maybe microwave radiation. The control processor coordinates the transmitters so that emitted electromagnetic radiation constructively interferes within a treatment volume while radiation passing through the rest of the subject randomly interferes or appears as noise. As a result, in a volume in which the electromagnetic radiation waveforms arrive in phase the power of all the transmitters add constructively resulting in a significant temperature rise, while the rest of the subject is exposed to a much lower average power level and thus a lower temperature rise.

9 Claims, 10 Drawing Sheets

THERMAL TREATMENT SYSTEM UTILIZING CONSTRUCTIVELY INTERFERING ELECTROMAGNETIC RADIATION

FIELD OF THE INVENTION

The present invention relates generally to medical treatment systems and more particularly to a medical treatment system employing radiofrequency radiation to thermally treat tissues.

BACKGROUND

Thermal treatment is used for treating a number of medical conditions, from sports injuries to infections to cancer. In a typical thermal treatment, thermal energy is applied to a subject's tissues in order to raise their temperature a few degrees above normal body temperature. Many types of pathogens and diseased cells are killed or are rendered vulnerable to medicines (e.g., chemotherapy) or the body's own immune system when exposed to higher temperatures. One form of thermal treatment involves applying heat to the body's exterior in the vicinity of the area to be treated, such as by applying heating blankets or heating units. However, such treatments heat all tissues in the vicinity of the applied heat, and thus may adversely affect surrounding healthy tissue. Another form of thermal treatment heats tissues within a body by exposing them to microwave radiation which raises the temperature of tissues by exciting water molecules within them, much as a microwave oven does to food. However, this thermal treatment method heats all tissues within the path of the microwave radiation, and thus also can adversely affect surrounding healthy tissues.

Another commonly used method for treating tissues within a body involves exposing the tissue to ionizing radiation, such as X-rays and gamma rays. As is well-known, tumors are frequently treated by exposing the tumor tissue to a series of narrow X-ray or gamma-ray beams, with each exposure made at several different exposure angles. This process exposes the tumor tissue at the convergence of the several beams to a high dose of radiation while exposing the rest of the body to a lower total dose (i.e., approximately the dose associated with a single beam exposure).

In addition, such methods require careful positioning and calibration of the emitter(s), with many high precision moving parts. While such treatment methods can be highly effective, such multibeam methods cannot be applied to thermal treatments employing microwave radiation since the objective in thermal treatments is to raise the tissue temperature for a period of time which requires continuous exposure to the microwave radiation.

SUMMARY

Various embodiments provide methods and systems for thermally treating a portion of a subject using microwave or other electromagnetic radiation without harming other portions of the subject. The various embodiments enable thermal treatments to be accomplished deep within a subject without exposing the rest of the subject's tissue or material to elevated temperatures.

In an embodiment, a plurality of electromagnetic radiation transmitters are positioned in known locations within a thermal treatment system and coupled to a control processor. The control processor is configured to control the transmissions of each of the transmitters in a coordinated manner such that emitted electromagnetic radiation constructively interferes within a desired treatment volume. By configuring the emitted waveform and the time delay or relative phase lag of the electromagnetic radiation emitted by each transmitter, the radiation constructively interferes in the volume where thermal treatment is desired while electromagnetic radiation passing through the rest of the subject appears as noise. As a result, a significant amount of thermal energy can be deposited within the volume of treatment, while the remainder of the subject is exposed to lower average power levels and thus experiences a lower rise in temperature. In some embodiments the electromagnetic radiation is microwave radiation, particularly embodiments used to thermally treat water-bearing materials such as living tissue. In an embodiment, electromagnetic radiation may be emitted in the form of short pulses which are emitted from each transmitter at individually determined times so that all the pulses arrive in the volume of treatment simultaneously. In another embodiment, microwave radiation is submitted in a pseudorandom waveform by all microwave transmitters with a time delay or phase lag so that the waveforms constructively reinforce each other in the volume of treatment while appearing as random noise throughout the rest of the subject. In an embodiment, the pseudorandom waveform may be similar to that used in a code division multiple access (CDMA) communications system.

BRIEF DESCRIPTION OF THE DRAWINGS

The accompanying drawings, which are incorporated herein and constitute part of this specification, illustrate exemplary aspects of the invention. Together with the general description given above and the detailed description given below, the drawings serve to explain features of the invention.

DETAILED DESCRIPTION

Figure 1:
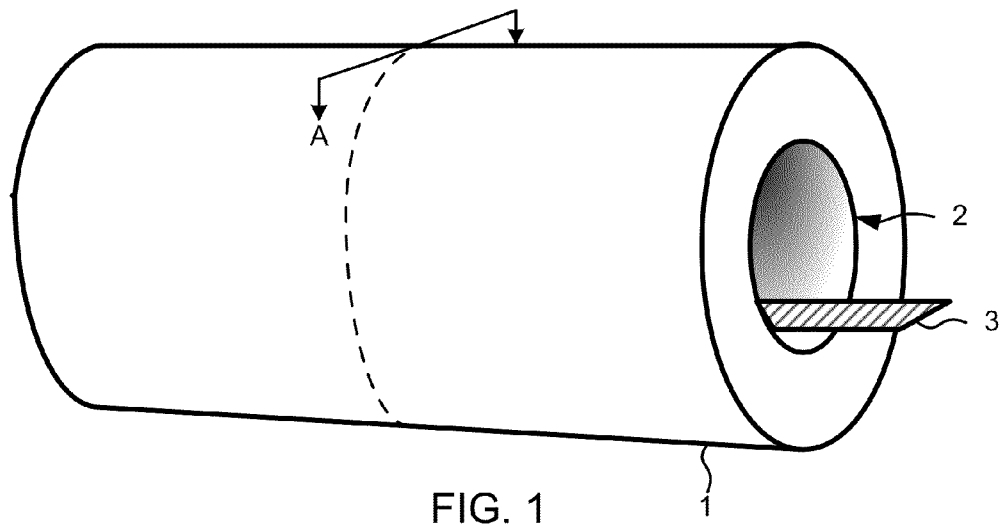
FIG. 1 is an illustration of an example thermal treatment system implementation of the present invention.

Various aspects will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

As used herein, the term "thermal treatment" is intended to encompass any process in which at least a portion of a body or material is heated by the deposition or application of thermal energy. As used herein, the terms "microwave" and "microwave radiation" refer to electromagnetic radiation which has the potential for depositing thermal energy within a body, such as to raise its temperature, but is not intended to reflect a particular frequency or wavelength. In a particular embodiment, microwave radiation of a frequency or wavelength that will excite water molecules is used in order to thermally treat living tissue, such as tissues of a human subject. However, other wavelengths or frequencies of electromagnetic radiation may be used when treating other types of materials, such as frequencies which excite various thermal vibrations within the material.

While the various aspects are illustrated with reference to a medical treatment system suitable for treating human patients, the present invention has broader applications, including nonhuman subjects and thermal treatment of non-living materials. Therefore, references to "patient," "subject," and "tissue" are intended to encompass both human and nonhuman treatment applications. Further, the term "thermal treatment" is intended to encompass any application of the various embodiments in order to deposit heat or raise the temperature of a living or nonliving material.

In overview, in an example embodiment a plurality of microwave transmitters are positioned in known locations within a thermal treatment system and coupled to a control processor. The control processor is configured to control the transmissions of each of the transmitters in a coordinated manner so that emitted electromagnetic radiation converges on and arrives at a desired treatment volume so that constructive interference of the radiation occurs within that volume. By configuring the emitted waveform and the time delay or relative phase of the electromagnetic radiation emitted by each transmitter, the radiation constructively interferes in the volume where thermal treatment is desired while electromagnetic radiation passing through the rest of the subject or material randomly interferes. As a result, a large amount of thermal energy is deposited within the volume of treatment, while the remainder of the subject is exposed to a much lower average power level and thus experiences a much lower rise in temperature. By coordinating the application of electromagnetic radiation, such as microwave radiation, in this manner (i.e., causing constructive interference at the point of treatment), thermal treatments can be accomplished deep within a subject without raising the rest of the subject's tissue or material to high temperatures. In one embodiment, electromagnetic radiation is emitted in the form of short pulses which are emitted from each transmitter at individually determined times so that all the pulses arrive in the volume of treatment simultaneously. In another embodiment, a pseudorandom waveform is emitted by all microwave transmitters with a time delay or phase lag such that the waveforms constructively reinforce each other in the volume of treatment while appearing as random noise throughout the rest of the subject or material. In this embodiment, the pseudorandom waveform may be similar to that used in a code division multiple access (CDMA) communications system.

In an embodiment, a plurality of relatively low-power microwave transmitters are positioned about the periphery of a volume in known locations with the volume configured to accept a subject (such as a patient, structure or volume of material) for thermal treatment. As illustrated in FIG. 1, such a system may include a structure for containing a subject to be treated which may be open or closed and, in an embodiment, may be in the form of a cylinder 1 with an interior surface defining an interior volume 2 into which a patient or subject may be positioned, such as on a movable table 3. In this example, the external appearance of the thermal treatment system may resemble that of magnetic resonance imaging (MRI), computer aided tomography (CAT) imaging or positron emission tomography (PET) imaging systems. However, the thermal treatment system employs very different technologies.

Figure 2:
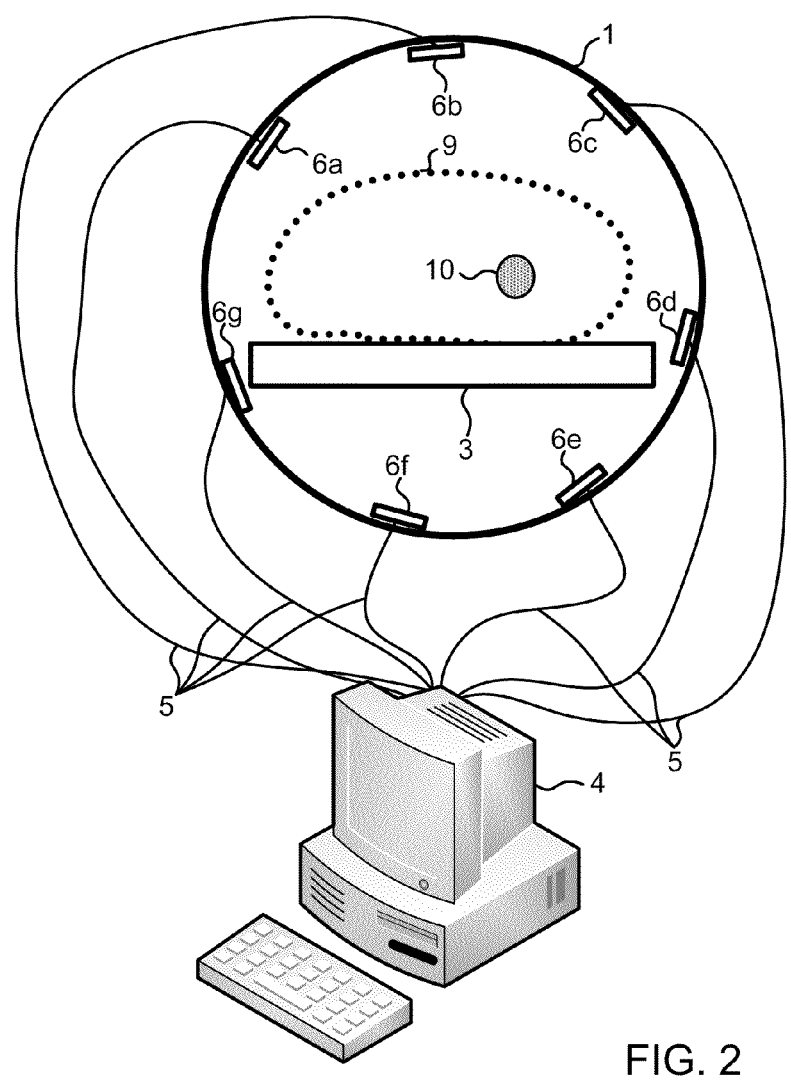
FIG. 2 is a system block diagram of a portion of a thermal treatment system including a cross-sectional view of the system illustrated in FIG. 1.

FIG. 2 illustrates a cross-sectional view of the cylinder 1 showing a portion of the system components of a thermal treatment system. This cross section view illustrates how in an embodiment a plurality of transmitters 6a-6g may be positioned around the circumference of the interior volume 2. A subject for treatment 9 may be positioned on a table 3 for thermal treatment of an interior volume for treatment 10, such as a tumor. The plurality of transmitters 6a-6g may be coupled to and controlled by a computer processor housed, for example, within a workstation or desktop computer 4 via a number of connections, such as cables 5. The plurality of transmitters 6a-6g may transmit any frequency of electromagnetic radiation. In a preferred embodiment the transmitters transmit microwave radiation which is suitable for thermally treating water bearing materials, such as tissue. For simplicity of description, the transmitters 6a-6g are referred to in the descriptions below as being microwave transmitters. However such references are not intended to imply that the embodiments are necessarily limited to microwave radiation. Also, the transmitters can be distributed in three-dimensional space even though FIG. 2 shows them arranged in a plane.

Figure 3:
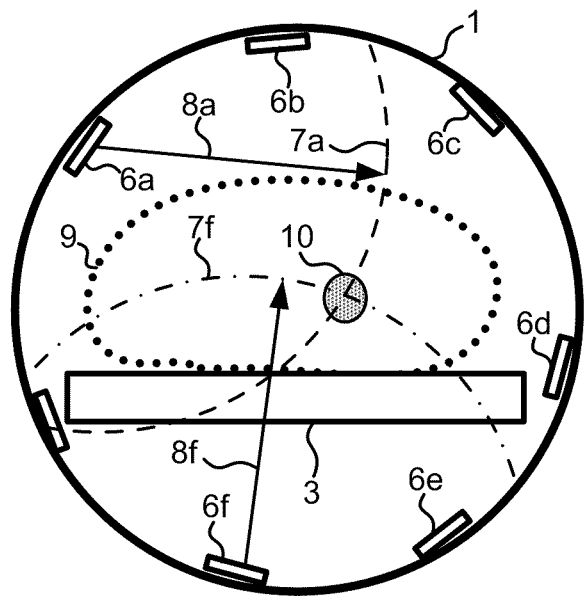
FIG. 3 is a cross-sectional diagram of a thermal treatment system illustrating an intersection of two microwave radiation wave fronts within a tumor.

The concept of constructive interference of electromagnetic radiation (e.g., microwave radiation) within a treatment volume implemented in the various embodiments is illustrated in FIG. 3. This figure shows a cross-section of the thermal treatment system 1 including a plurality of microwave transmitters 6a-6g positioned around a subject 9. When a microwave pulse is emitted from one transmitter, such as transmitter 6a, the pulse travels outward at the speed of light as a wave front 7a. Thus, within a given amount of time the microwave radiation travels a determinable distance 8a. In FIG. 3 the emitted a wave front 7a has intersected the volume for treatment 10 which is a distance 8a from the transmitter 6a. Similarly, radiation emitted from another transmitter 6f will travel a different distance 8f to reach the volume for treatment 10. If the microwave transmissions are properly timed, the wave fronts 7a, 7f from each of the transmitters at 6a, 6f will arrive simultaneously in the treatment volume 10.

Figure 4:
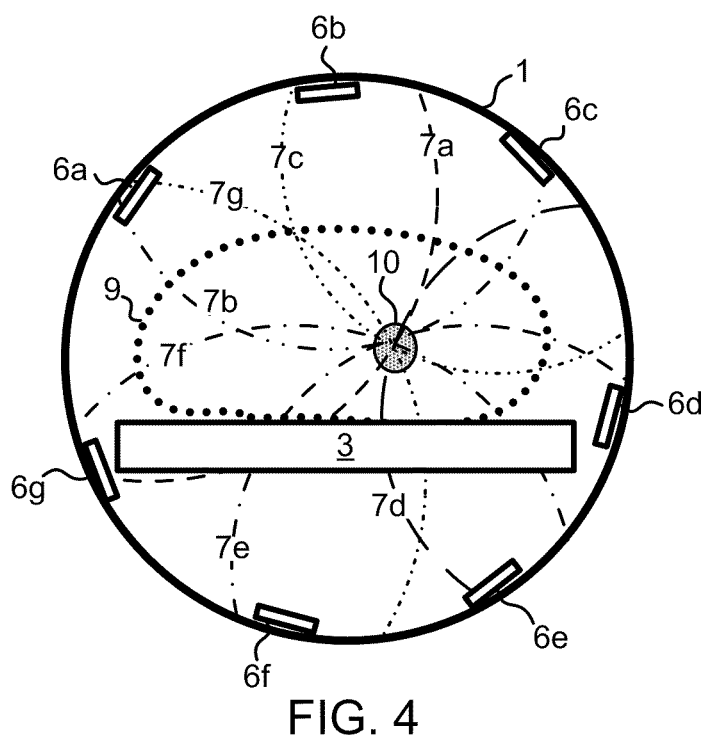
FIG. 4 is a cross-sectional diagram of a thermal treatment system illustrating intersection of several microwave radiation wave fronts within a tumor.

This concept may be employed to concentrate a significant amount of microwave radiation within the treatment volume 10 by using several microwave transmitters 6a-6g as illustrated in FIG. 4. As FIG. 4 illustrates, wave fronts from a plurality (e.g., seven) of microwave transmitters 6a-6g can be coordinated to arrive simultaneously so the wave fronts or pulses overlap in the treatment volume 10. The figure also illustrates that in the rest of the subject 9 there are points where a few wave front will also intersect. For illustrative purposes FIG. 4 shows seven microwave transmitters 6a-6g, but in various implementations fewer or more transmitters may be used. As FIG. 4 illustrates, the region of treatment will typically be offset from the centerline of the system 1, and may be at any location within the interior volume 2. Nevertheless simultaneous arrival of wave fronts 7a-7g can be achieved by controlling the timing or phase lag of the pulses emitted from each of the transmitters 6a-6g.

Figure 5A:
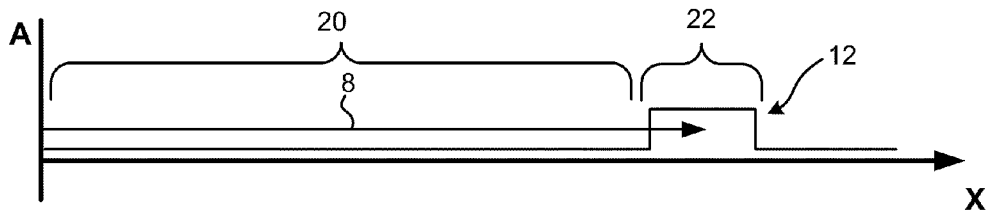
FIGS. 5A and 5B are graphs of microwave radiation amplitude versus position illustrating microwave pulses according to an aspect of the present invention.

A variety of wave forms may be implemented in the various embodiments to achieve the desired concentration of microwave energy within the volume of treatment 10. FIG. 5A illustrates one approach in which the microwave energy is emitted in the form of discrete pulses 12. Such pulses may be of a brief duration as shown in the portion 22 separated by extended durations of little or no transmitted energy as shown in the portion 20. Since the microwave pulse travels at the speed of light, its shape can be represented graphically as amplitude vs. time (not shown) or amplitude vs. distance from the transmitter as shown. In the amplitude vs. distance representation in FIG. 5A, the pulse 12 is shown for illustrative purposes at the instant when the pulse has traveled the distance 8 between the transmitter 6 and the volume for treatment 10. This figure shows the wave form as it would appear along the direct line between the transmitter and the volume of treatment 10 at that particular instant. This illustrates how at that instant when the pulse has traveled the distance 8 from the transmitter to the volume of treatment 10 the pulse width portion 22 spans the volume for treatment 10, depositing energy in the volume, while the rest of the volume portion 20 is receiving little energy. Of course, the transmission of the pulse 12 through the subject will result in the same energy deposition along the path of energy propagation when averaged over time.

Figure 5B:
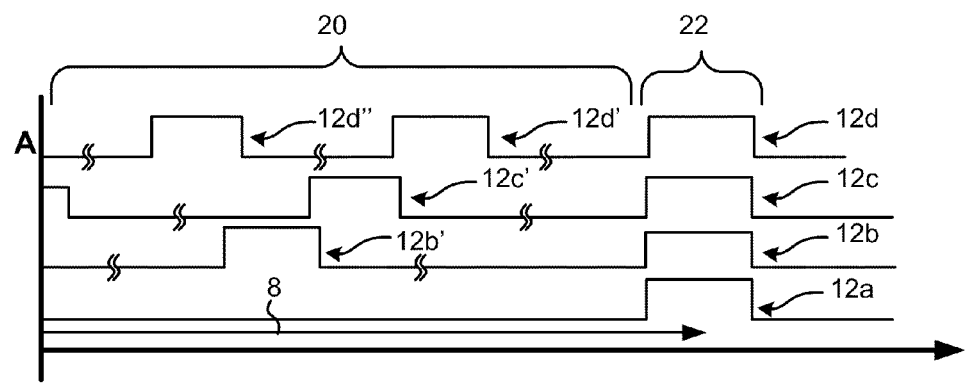

FIG. 5B also illustrates the wave form in an amplitude vs. distance representation at the same instant as illustrated in FIG. 5A including pulses emitted from other transmitters. The distance from each transmitter to the volume of treatment 10 will be different (see FIGS. 3 and 4). However, by emitting pulses from each transmitter with the proper timing or phase lag, all of the pulses can be configured to arrive simultaneously at the volume of treatment 10 as illustrated at portion 22. The timing of the pulse transmissions from each transmitter will depend upon the distance between that transmitter and the volume of treatment 10 and the speed of light traveling between those two points (i.e., the speed of light through air and through the subject as described more fully below with reference to FIG. 13). If the pulses are all emitted with the proper timing, the energy within each pulse will be added together to deposit substantially more energy in the volume of treatment 10 than the remainder 20 of the subject. Pulses from each transmitter pass through the remainder of the subject portion 20, but because different paths traversed, and thus the distances traveled, are different the pulses do not coincide (i.e., pass through the same point at the same instant). This is illustrated in FIG. 5B by the manner in which other pulses 12b', 12c', 12d' and 12d'' do not coincide within the remainder of the volume portion 20 along the direct path (distanced 8) between one transmitter and the volume of treatment 10.

Figure 6:
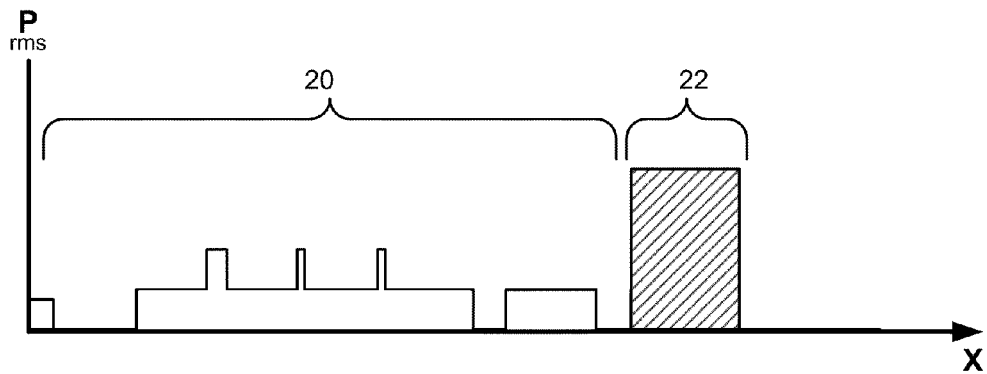
FIG. 6 is an illustrative graph of power versus position illustrating the cumulative power of the microwave pulses illustrated in FIG. 5B.

The energy deposited within the subject at any given instant is proportional to the sum of the pulses as illustrated in FIG. 6. As illustrated, in the volume of treatment 10 where the pulses coincide (portion 22), the energy deposited in that volume at the instant the pulses overlap and constructively reinforce greatly exceeds the energy deposited at that instant in the remainder of the subject portion 20. At any given instant, the remainder of the volume portion 20 will receive no energy, the energy of a single pulse, or occasionally the energy of two overlapping pulses. The spikes of overlapping pulses within portion 20 in FIG. 6 reflect the points where two pulse wave fronts intersect in FIG. 4. While FIG. 6 shows the energy deposited at a brief instant in time, if pulses are emitted frequently in the manner described above, the time averaged energy deposition within the subject will resemble the graph shown in FIG. 6. For example, if the distance 8 from one transmitter to the volume of interest is D, then pulses could be emitted with a frequency of approximately f=c/D, where c is the speed of light. This high frequency pulse rate would result in a time average deposition of energy similar to the graph in FIG. 6.

Figure 7A:
FIG. 7A is an amplitude versus time illustration of a microwave pseudorandom waveform suitable for use in various aspects of the present invention.

FIG. 7A illustrates another wave form that may be implemented in which pulses are emitted in a pseudorandom pattern that will add constructively in the volume of treatment 10 (portion 22), but randomly interfere or otherwise appear as noise in the remainder of the subject (portion 20). This waveform may implement the type of pseudorandom wave forms implemented in code division multiple access (CDMA) cellular communication systems. As is well known, CDMA communication technologies modulate information on a pseudorandom waveform with each communication link assigned a pseudorandom number offset. By offsetting the pseudorandom wave forms of multiple communication links in this manner, several communication links can be established in the same area within the same frequency band, since the various signals appearing like noise to each receiver. CDMA communications relies upon demodulating the received signals using the pseudorandom number offset of a particular communication device to resolve that signal from the others. In the present invention, the pseudorandom wave form concept is used with each transmitter offset in time so that the various waveforms will constructively reinforce in the volume of treatment 10. The different path lengths from transmitters to all points within the subject outside the volume of treatment 10 ensures that the emitted energy arrives at each point outside that volume with the signals offset by different amounts. This waveform offset due to path length differences ensures that the microwave energy outside the volume of treatment 10 has the appearance of noise. Thus, pulses are as likely to destructively interfere as constructively interfere. As a result, a low average power (root mean square) is applied to the subject outside the volume of treatment 10 while a high average power level is applied within the volume of treatment 10.

Figure 7B:
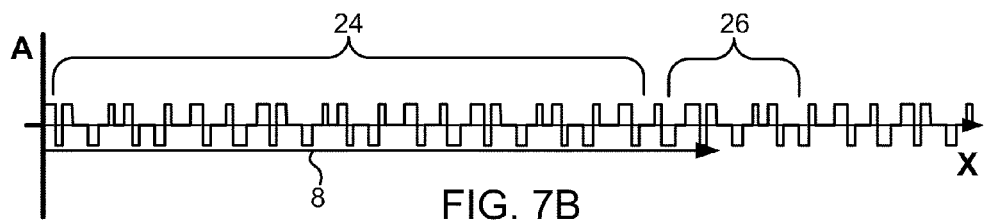
FIG. 7B is an amplitude versus position illustration of the microwave pseudorandom waveform illustrated in FIG. 7A.
Figure 7C:
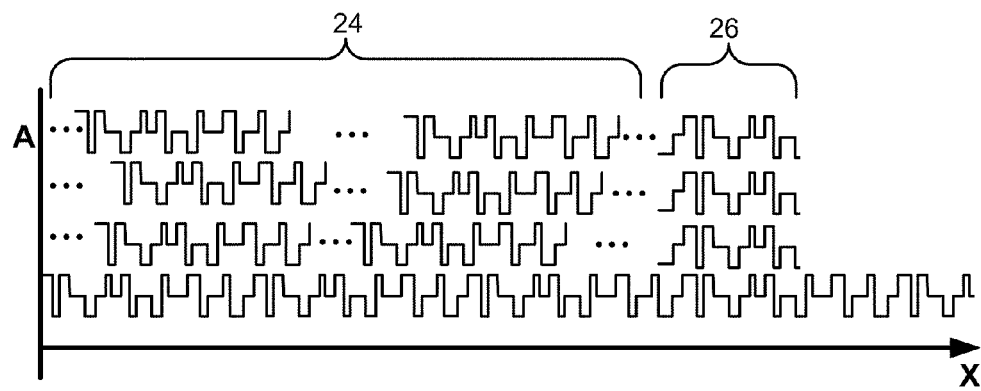
FIG. 7C is an amplitude versus position illustration of four pseudorandom waveform microwave radiation signals.
Figure 8:
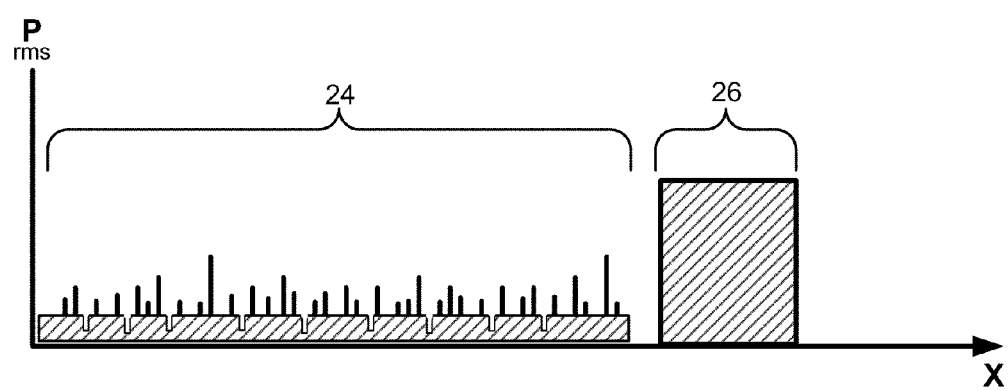
FIG. 8 is a graph of power versus position illustrating the cumulative power resulting from the combination of the microwave pseudorandom waveforms illustrated in FIG. 7C.

This effect is illustrated in FIGS. 7A-7C and 8. FIG. 7A illustrates a pseudorandom waveform emitted from a single transmitter as amplitude versus time. Since microwave radiation travels at the speed of light, the waveform may also be presented as amplitude versus distance along a path of propagation X as illustrated in FIG. 7B. This figure illustrates how the waveform within the volume of treatment 10, portion 26, which is distance 8 from the transmitter, may appear very similar to the waveform within the rest of the subject, portion 24. The combined effect of several wave forms emitted from a number of transmitters coordinated so that the waveforms constructively interfere within the volume of treatment 10 is illustrated in FIG. 7C. This figure shows microwave transmissions that have been emitted from four transmitters spaced apart within a system. Due to the coordination of the transmission timing or phase lag the four waveforms arrive in the volume of treatment 10, portion 26, in phase so that their waves, and thus their deposited energies, constructively reinforce each other. This increases the power deposited in this volume as illustrated in portion 26 shown in FIG. 8. In the rest of the subject, portion 24, the different waveforms are out of phase due to the different distances traveled from each transmitter to each point. This is shown in FIG. 7C by the illustrated shift in the wave forms due to the different path lengths travel to each point along the path X. As a result of the pseudorandom waveform and the various microwave transmissions being out of phase, the combinations of all microwave waveforms has the characteristic of noise. Thus, the sum of all microwave transmissions within the subject outside the volume of treatment 10 exhibits a low level average power deposition with some local instantaneous spikes and dips in power as illustrated in portion 24. By increasing the number of transmitters and reducing the power transmitted by each transmitter, the ratio of the average power density applied within the volume of treatment 10, portion 26, to the average power density applied within the rest of the subject, portion 24, can be increased. In this manner, the total power applied to a volume of treatment 10, and thus the temperature within that volume, can be increased to effective levels without adversely impacting the rest of the subject, portion 24.

Figure 9A:
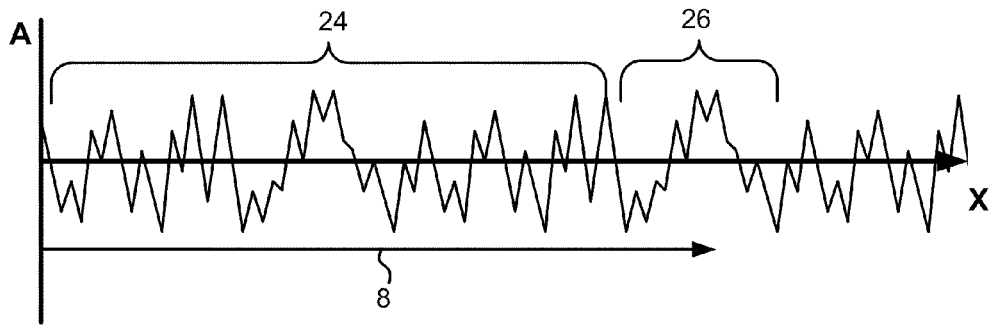
FIG. 9A is an amplitude versus position illustration of a different microwave pseudorandom waveform suitable for use in various aspects of the present invention.
Figure 9B:
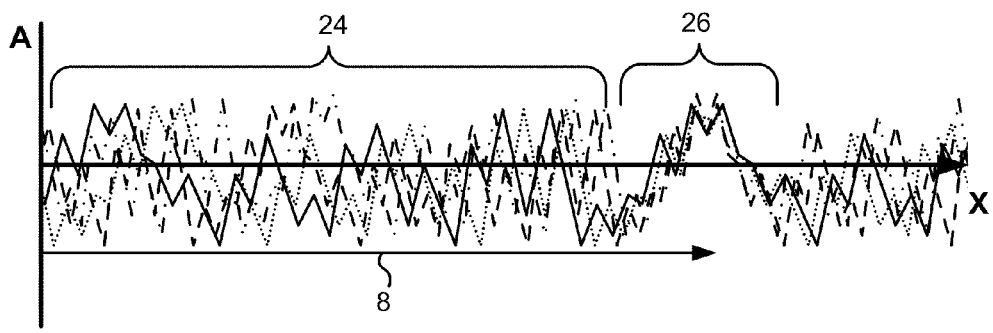
FIG. 9B is an amplitude versus position illustration of four pseudorandom waveform microwave radiation signals similar to those illustrated in FIG. 9A.
Figure 10:
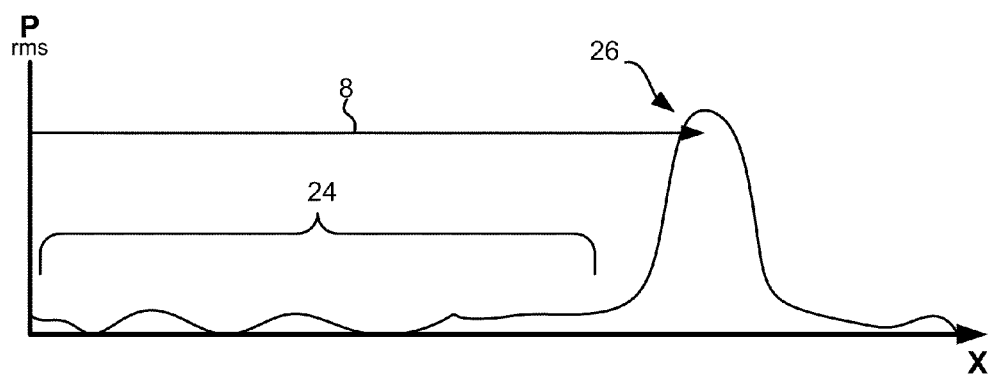
FIG. 10 is a graph of power versus position illustrating the cumulative power resulting from the combination of the microwave pseudorandom waveforms illustrated in FIG. 9B.

The microwave waveform emitted by transmitters is not limited to the square wave shapes illustrated in FIGS. 6A-B and 7A-C, as any microwave waveform that have pseudorandom characteristics may be used. This is shown in FIGS. 9A-9B and 10 which illustrate a more random and multifrequency waveform. As described above with reference to FIG. 7B, the pseudorandom waveform within the volume of treatment 10, portion 26, may appear very similar to the waveform within the rest of the subject, portion 24, as illustrated in FIG. 9A. The combined effect of several waveforms emitted from a number of transmitters coordinated so that the waveforms constructively interfere within the volume of treatment 10 is illustrated in FIG. 9B. By coordinating transmission phasing the four illustrated waveforms arrive in the volume of treatment 10, portion 26, in phase so that the waves, and thus their deposited energies, constructively reinforce each other. This increases the power deposited in this volume as illustrated in portion 26 shown in FIG. 10. In the rest of the subject, the different waveforms are out of phase and thus deposit a much lower amount of energy in portion 24.

By controlling the nature of the pseudorandom waveform and the relative phasing of transmissions from each of the various transmitters, the size of the volume of treatment 10 and the energy deposited within that volume can be precisely controlled. Additionally, the number of transmitters transmitting microwave energy may be varied in order to adjust the size of the volume of treatment 10 and the maximum-to-minimum energy deposition ratio.

As mentioned above, the various embodiments may be applied to a variety of applications in which energy, particularly heat energy, needs to be deposited within a limited volume of a subject (e.g. patient, structure, or material). While the particular frequency or wavelength of radiation employed will depend upon the material being treated, the fundamental operational concepts are substantially similar. Therefore, in order to simplify the description of the various embodiments, the following description of example methods focuses on a medical treatment application involving thermal treatment of a tumor within a patient. The tumor in this example constitutes the volume of treatment 10 and the subject is a patient 9.

Figure 11:
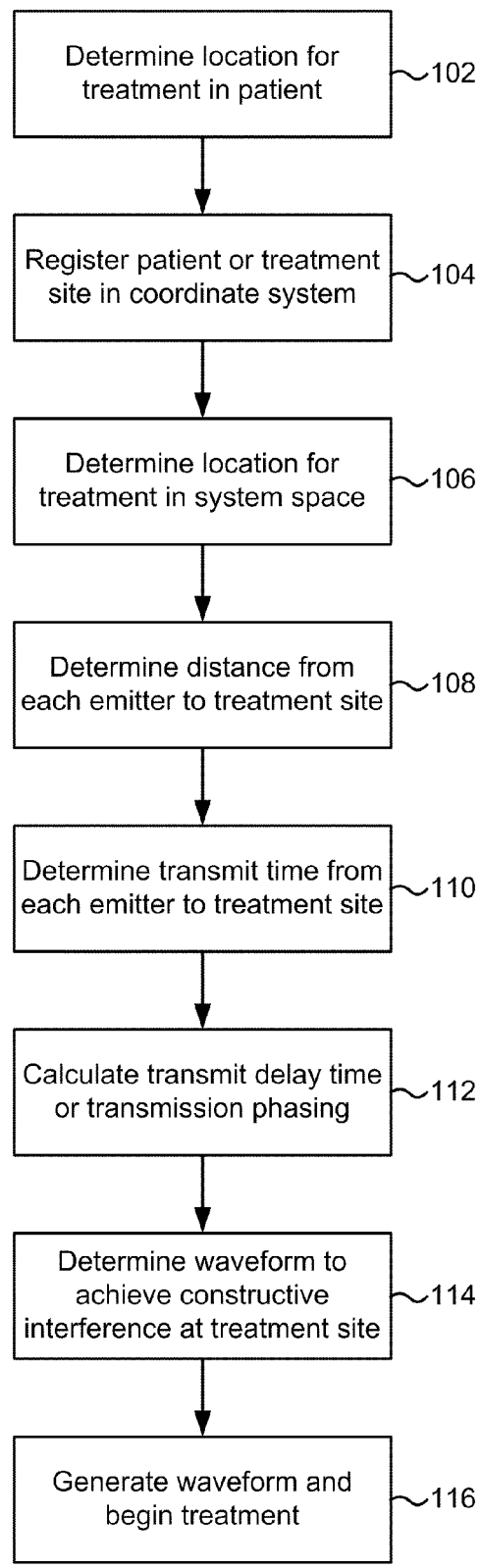
FIG. 11 is a process flow diagram illustrating an example method for thermally treating a patient according to an aspect of the present invention.

FIG. 11 illustrates an example method which may be implemented within a thermal treatment system according to an embodiment. In order to thermally treat a patient's tumor, the precise location of the volume to be treated within patient must be determined, step 102. Methods for locating tumors and other volumes for treatment within patients are well known in the medical arts, including the CAT, PET and MRI scanning technologies and systems. Such 3-D imaging systems can generate the 3-D coordinates of a tumor within a coordinate system related to the patient's body. This coordinate information can be used to determine the location of the tumor within the thermal treatment system 1 by determining the location of the patient within the system, step 104. This process of locating a first coordinate system for the tumor within a second coordinate system for the thermal treatment system 1 is referred to as "registration." In some implementations, the location of the tumor may be determined with respect to an external reference (referred to as an external coordinate system), such as a table or support platform on which the patient is resting when the 3-D imaging of the tumor was performed. In that case, the external coordinate system will be registered with the coordinate system of the thermal treatment system 1. The registration process permits a system computer to accurately determine the position of the tumor or volume for treatment within the thermal treatment system 1 using simple geometric transformations, step 106. The mathematical transformations used to determine the location for treatment within the system's coordinate system are well-known in the medical arts related to computer-aided surgery and 3-D imaging.

With the location of the tumor within the thermal treatment system 1 determined, the system can determine the distance from each microwave transmitter to the treatment site, step 108. As described more fully below with reference to FIG. 12, this operation involves simple geometric calculations. With the transmitter-to-tumor distance determined, the system may also determine the transit time for microwave pulses traveling between each transmitter and the tumor site, step 110. As described more fully below with reference to FIG. 13, this calculation may involve accounting for differences in the speed of light within air and tissues. Using the determined transit time for each transmitter, the system can calculate the particular transmission delay or phase lag that should be applied to each transmitter so that all transmitted energy arrives within the tumor in phase, step 112. This operation involves simple linear calculations. Depending upon the type of thermal treatment desired and the volume to be treated, the system may also determine the waveform encoding to apply in order to achieve the desired degree of constructive interference within the treatment volume, step 114. This may involve determining a particular type of pseudorandom waveform or encoding a pulse within a pseudorandom waveform similar to the manner in which CDMA communication systems encode communication information. Finally, a thermal treatment begins by transmitting the microwave energy from the various transmitters using the calculated time delay or phase lag, step 116. Treatment may continue in order to maintain the tumor at a desired elevated temperature (as controlled by the power level admitted by all of the transmitters) for a required duration.

Figure 12:
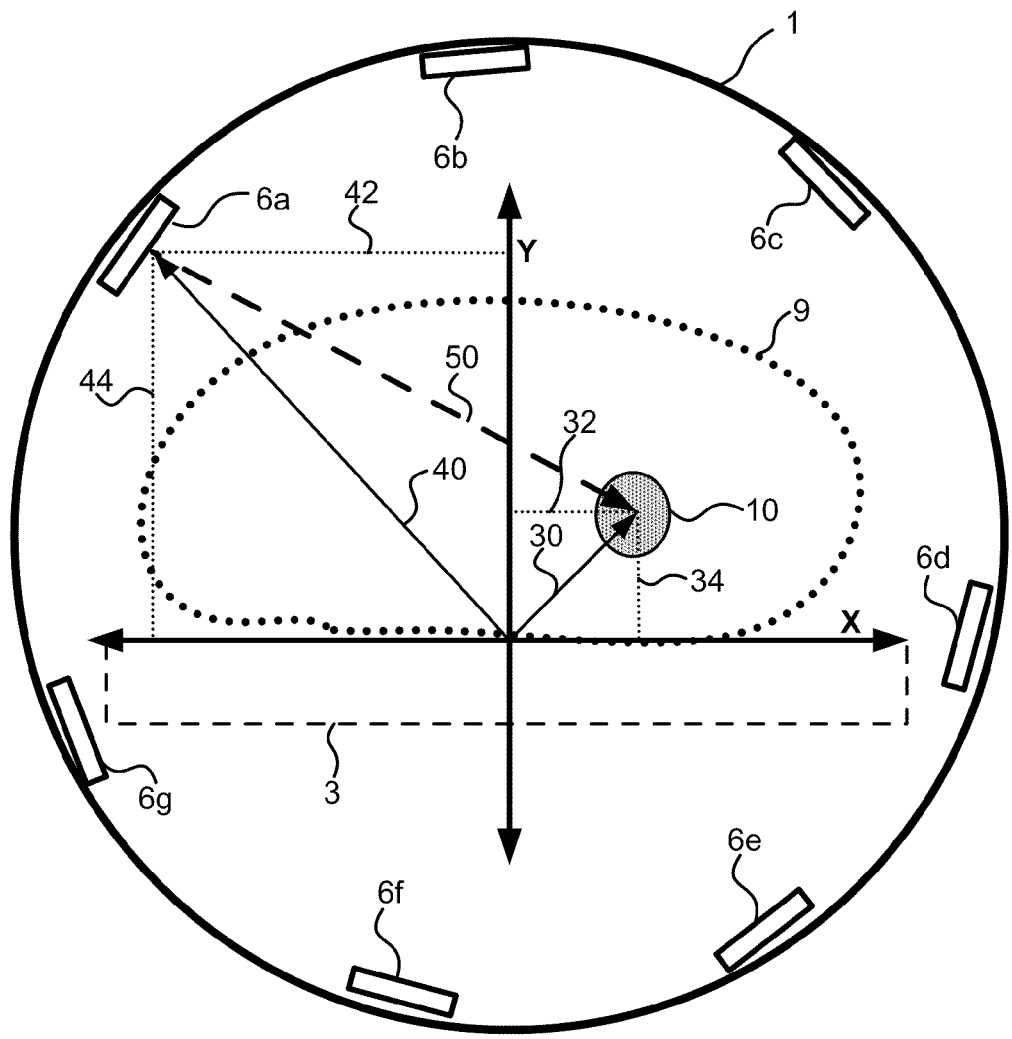
FIG. 12 is a cross-sectional diagram of a thermal treatment system illustrating geometric calculations involved in the method illustrated in FIG. 11.

As mentioned above, the process of determining the distance from each transmitter to the volume of treatment 10 involves simple geometric calculations. FIG. 12 illustrates an example of such calculations for determining the distance from one transmitter 6a to a tumor 10 within a thermal treatment system 1. In this example, the location of the tumor 10 is known in a coordinate system based upon the table 3 on which the subject 9 lies. In particular, the center point of the tumor 10 lies at a distance 32 along the X coordinate, which is parallel to the surface of the table 3, and at a distance 34 along the Y coordinate, i.e., above the table 3. These calculations are readily generalized to a three-dimensional system of coordinates and emitters. A computer processor of the thermal treatment system 1 may be informed of the location of the table 3 by design, sensor (not shown) or operator inputs so the processor can correlate coordinate calculations (which may be performed in the systems coordinate system) with the X and Y coordinates of the table 3. For example, the computer processor may be informed that the transmitter 6a is positioned a distance 42 along the X axis and distance 44 along the Y axis from the coordinate axis of the table 3. As such, the system can determine the distance 40 from the transmitter 6a to the coordinate axis. The computer processor can also determine the distance 30 from the coordinate axis to the tumor 10, which is simply the square root of the sum of the squares of the tumor's X and Y coordinates (i.e., distances 32 and 34). Since the computer processor knows the distance 40 from the transmitter 6a to the coordinate axis, the system can easily calculate the distance 50 from the transmitter to the tumor 10 as the square root of the sum of the squares of the two distances 30 and 40.

Figure 13:
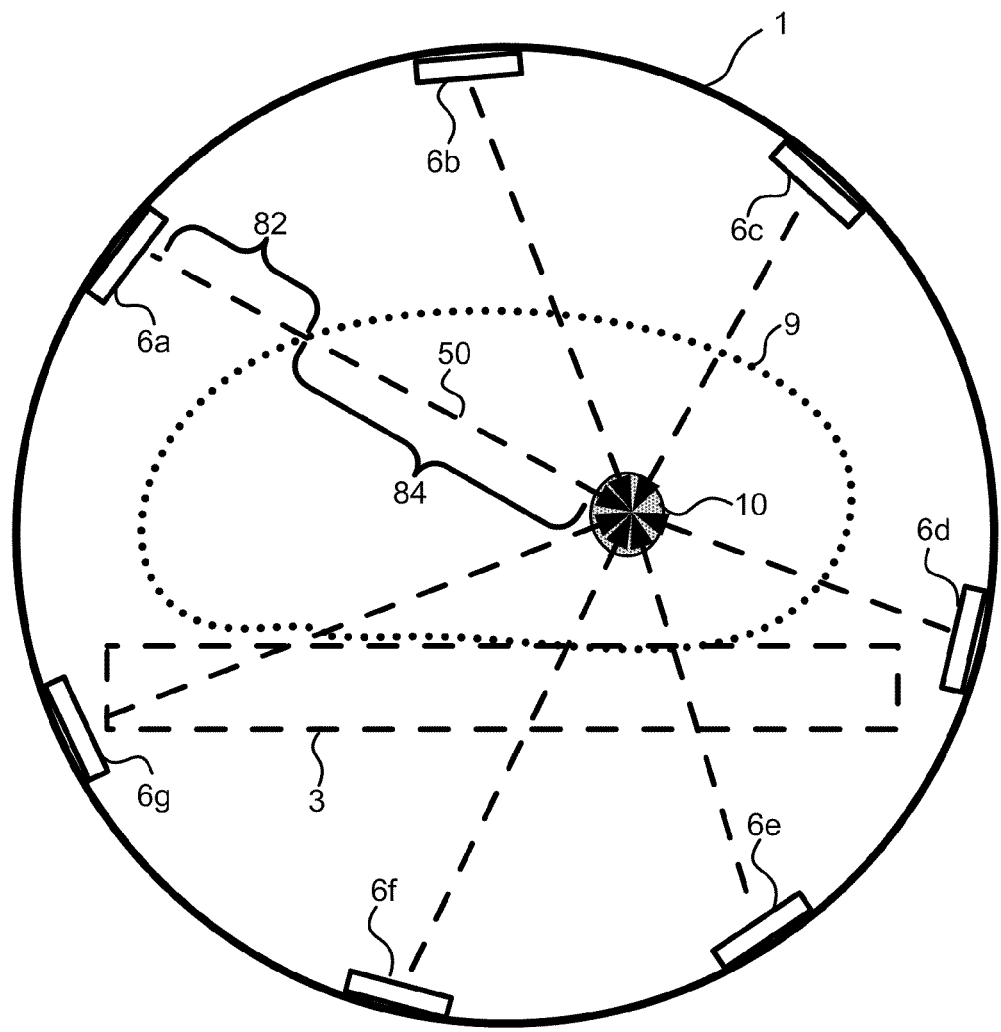
FIG. 13 is a cross-sectional diagram of a thermal treatment system illustrating calculations involved in the method illustrated in FIG. 11 taking into account the effects of tissue on the propagation of microwave radiation.

If the distance 50 between the transmitter 6a and the tumor 10 was filled with air, the time of transit would simply be the distance 50 divided by the speed of light in air. However, as illustrated in FIG. 13, in most applications the distance 50 will be filled partly with air, portion 82, and partly with the material of the subject, such as tissue, portion 84. Therefore, to accurately determine the transit time or time of arrival at the tumor 10 of microwave energy emitted from each transmitter 6a-6g, the computer processor can calculate the distances between the transmitters and the outer surface of the subject 9 as well as the distances along the line between each transmitter and the tumor 10 within the subject 9. Such calculations can easily be performed by a system computer processor informed of the 3-D coordinates of the subject 9 and the tumor 10 (e.g., from a 3-D imaging scan) using simple geometric calculations similar to those described above with reference to FIG. 12. The calculation of the transit time thus involves determining the distance traveled by the emitted electromagnetic (e.g., microwave) radiation through air and dividing that distance by the speed of light in air to obtain the first transit time portion (i.e., the time to travel portion 82), determining the distance traveled by emitted electromagnetic radiation through the subject on the way to the tumor 10 and dividing that distance by the speed of light in tissue (or whatever material comprises the subject) to obtain a second transit time portion (i.e., the time to travel portion 84), and adding the first and second transit time portions.

Figure 14:
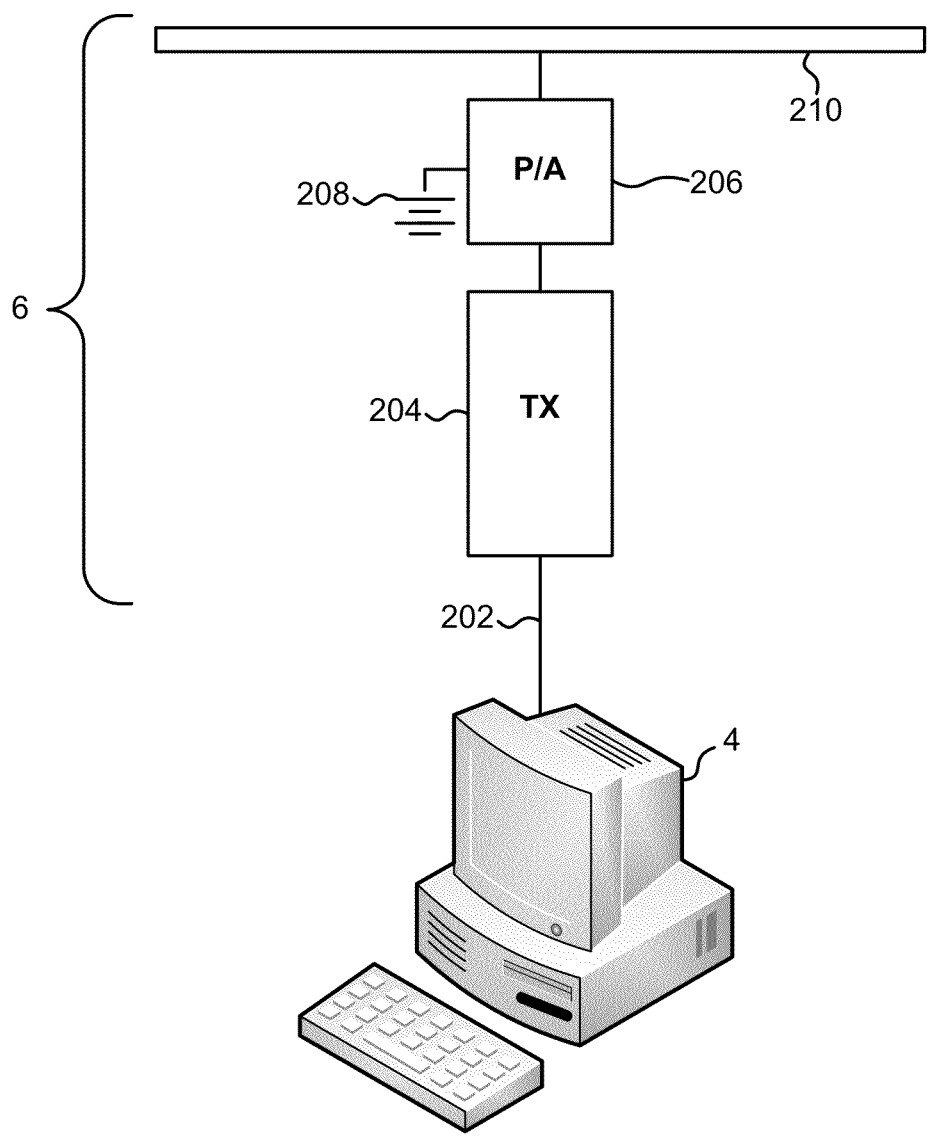
FIG. 14 is a component block diagram of a portion of a thermal treatment system according to an aspect of the present invention.

FIG. 14 illustrates a portion of the components of a thermal treatment system 1 according to an embodiment. A thermal treatment system 1 will include a control processor 260 which is configured with software instructions to perform operations such as those described above to control the overall power level and phase of the various transmitters. Control signals may be carried from the control processor 260 by cables 202 to individual waveform generators 204. Such waveform generators 204 may use circuitry similar to the transmitter circuitry implemented on CDMA cellular telephones. Such waveform generators 204 may include digital signal processors configured to generate a pseudorandom waveform such as described above with reference to FIGS. 7A-10. In order to output the power necessary to achieve desired thermal treatment power deposition levels, the waveform generator 204 may be coupled to a power amplifier 206 which can boost the transmitted power level using additional energy from a power source 208. The microwave energy output by the power amplifier 206 is coupled to an antenna, such as a microwave antenna 210, which is configured and positioned within the thermal treatment system 1 to radiate power in a suitable manner. In an embodiment, the waveform generator 204, power amplifier 206 and antenna 210 may be fabricated as a transmitter unit 6. By using integrated circuits and fabrication methods used for producing cellular telephone components, which are fixed in place with no requirement for aiming or focusing mechanisms, the transmitter units 6 may be produced cost effectively so that a thermal treatment system 1 can include a large number of transmitters while remaining affordable.

FIG. 14 illustrates a portion of the components of a thermal treatment system 1 according to an embodiment. A thermal treatment system 1 will include a control processor 261 housed, for example, within a workstation or desktop computer 4. The control processor may be configured with software instructions to perform operations such as those described above to control the overall power level and phase of the various transmitters. Control signals may be carried from the control processor 261 by cables 202 to individual waveform generators 204. Such waveform generators 204 may use circuitry similar to the transmitter circuitry implemented on CDMA cellular telephones. Such waveform generators 204 may include digital signal processors configured to generate a pseudorandom waveform such as described above with reference to FIGS. 7A-10. In order to output the power necessary to achieve desired thermal treatment power deposition levels, the waveform generator 204 may be coupled to a power amplifier 206 which can boost the transmitted power level using additional energy from a power source 208. The microwave energy output by the power amplifier 206 is coupled to an antenna, such as a microwave antenna 210, which is configured and positioned within the thermal treatment system 1 to radiate power in a suitable manner. In an embodiment, the waveform generator 204, power amplifier 206 and antenna 210 may be fabricated as a transmitter unit 6. By using integrated circuits and fabrication methods used for producing cellular telephone components, which are fixed in place with no requirement for aiming or focusing mechanisms, the transmitter units 6 may be produced cost effectively so that a thermal treatment system 1 can include a large number of transmitters while remaining affordable.

Figure 15:
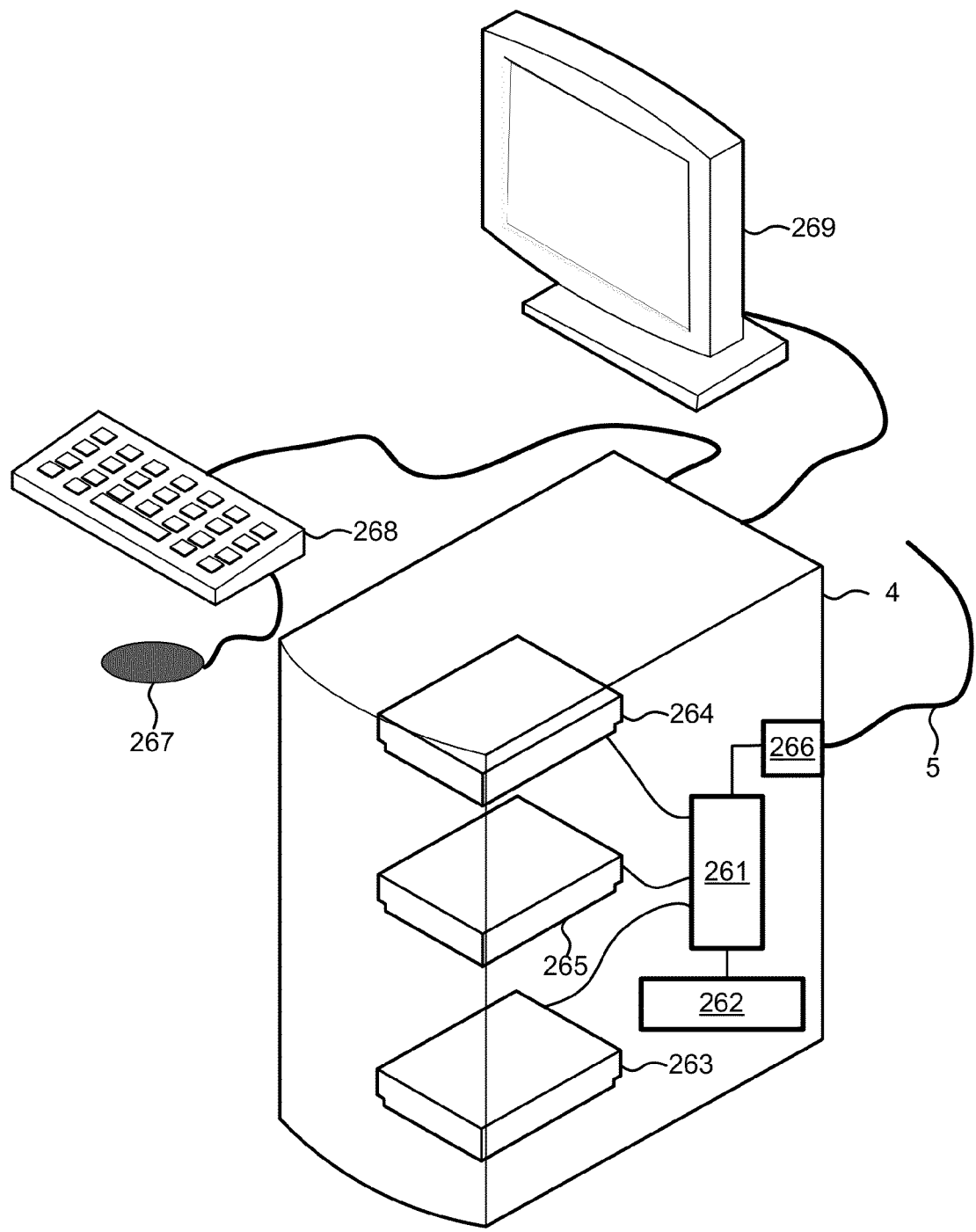
FIG. 15 is a component block diagram of a computing system suitable for use with an aspect of the present invention.

A thermal treatment system may include a control processor 261 housed within any of a variety of computing devices, such as a workstation computer 4 illustrated in FIG. 15. Such a workstation computer 4 typically includes the control processor 261 coupled to volatile memory 262 and a large capacity nonvolatile memory, such as a disk drive 263. The computer 4 may also include a floppy disc drive 264 and a compact disc (CD) drive 265 coupled to the processor 261. The computer 4 may also include a pointing device such as a computer mouse 267, a user input device such as a keyboard 268, and a display 269. The computer 4 may also include a number of connector ports 266 coupled to the processor 261 for connecting to cables 5 for connecting to the plurality of transmitters 6a-6g. The connector ports 266 may also couple the processor 261 to a network.

The various embodiments may be implemented by the computer processor 261 executing software instructions configured to implement the described methods. Such software instructions may be stored in memory 262, 263 as separate applications, or as compiled software implementing an embodiment method. Further, the software instructions may be stored on any form of tangible processor-readable memory, including: a random access memory 262, hard disc memory 263, a floppy disk (readable in a floppy disc drive 264), a compact disc (readable in a CD drive 265), electrically erasable/programmable read only memory (EEPROM), read only memory (such as FLASH memory), and/or a memory module (not shown) plugged into the computing device 4, such as an external memory chip or a USB-connectable external memory (e.g., a "flash drive") plugged into a USB network port 266.

The order in which the blocks of a method described above and shown in the figures is for example purposes only as the order of some blocks may be changed from that described herein without departing from the spirit and scope of the present invention and the claims.

The blocks of a method or algorithm described in connection with the aspects disclosed herein may be embodied directly in hardware, in a software module executed by a processor, or in a combination of the two. A software module may reside in processor readable memory which may be any of RAM memory, flash memory, ROM memory, EPROM memory, EEPROM memory, registers, hard disk, a removable disk, a CD-ROM, or any other form of storage medium known in the art. An exemplary storage medium is coupled to a processor such that the processor can read information from, and write information to, the storage medium. In the alternative, the storage medium may be integral to the processor. The processor and the storage medium may reside in an ASIC. The ASIC may reside in a user terminal or mobile device. In the alternative, the processor and the storage medium may reside as discrete components in a user terminal or mobile device. Additionally, in some aspects, the blocks and/or actions of a method or algorithm may reside as one or any combination or set of codes and/or instructions on a machine readable medium and/or computer readable medium, which may be incorporated into a computer program product.

The foregoing description of the various aspects is provided to enable any person skilled in the art to make or use the present invention. Various modifications to these aspects will be readily apparent to those skilled in the art, and the generic principles defined herein may be applied to other aspects without departing from the spirit or scope of the invention. Thus, the present invention is not intended to be limited to the aspects shown herein, and instead the claims should be accorded the widest scope consistent with the principles and novel features disclosed herein.

What is claimed is:

1. A system, comprising:
   a processor; and
   a plurality of electromagnetic radiation transmitters coupled to the processor, wherein the processor is configured with processor-executable instructions to perform operations comprising:
      determining a transit time of electromagnetic radiation emitted from each of the plurality of electromagnetic radiation transmitters and arriving within a volume for treatment within a subject; and
      based on the determined transit times, configuring and controlling each of the plurality of electromagnetic radiation transmitters to emit electromagnetic radiation having a pseudorandom waveform configured so that emitted electromagnetic radiation constructively interferes within the volume for treatment within a subject and randomly interferes outside the volume for treatment of a subject,
   wherein determining a transit time of electromagnetic radiation emitted from each of the plurality of electromagnetic radiation transmitters comprises:
      calculating a first transit time portion by dividing a first distance between each of the plurality of electromagnetic radiation transmitters and an outer surface of the subject by the speed of light in air;
      calculating a second transit time portion by dividing a second distance between the outer surface of the subject and the volume for treatment within the subject by the speed of light in tissues of the subject; and
      adding the first transit time portion and the second transit time portion.

2. The system of claim 1, wherein the processor is configured with software executable instructions to perform operations further comprising:
   calculating a phase lag for each of the plurality of transmitters that is used to control the emission of the electromagnetic radiation.

3. The system of claim 1, wherein each of the plurality of electromagnetic radiation transmitters is a microwave transmitter.

4. The system of claim 1, wherein:
   the structure comprises a cylinder having an interior surface defining an interior volume configured to contain the subject; and
   the plurality of electromagnetic radiation transmitters are positioned on and distributed about the interior surface.

5. A system, comprising:
   a plurality of means for emitting electromagnetic radiation;
   means for determining a time of arrival of the emitted electromagnetic radiation from each of the plurality of means for emitting electromagnetic radiation; and
   means for configuring and controlling, based on time of arrival, each of the plurality of means for emitting electromagnetic radiation to emit electromagnetic radiation having a pseudorandom waveform configured so that the emitted electromagnetic radiation from each of the plurality of means for emitting electromagnetic radiation constructively interfere within a volume for treatment within a subject and randomly interferes outside the volume for treatment of a subject,
   wherein means for determining the time of arrival comprises:
      means for calculating a first transit time portion by dividing a first distance by the speed of light in air, wherein the first distance comprises a distance between each of the plurality of means for emitting the electromagnetic radiation and an outer surface of the subject;
      means for calculating a second transit time portion by dividing a second distance by the speed of light in a material of the subject, wherein the second distance comprises a distance between the outer surface of the subject and the volume for treatment within the subject; and means for adding the first transit time portion and the second transit time portion.

6. The system of claim 5, further comprising:
means for calculating a phase lag for each of the plurality of means for emitting electromagnetic radiation that is used by the means for controlling.

7. The system of claim 5, wherein each of the plurality of means for emitting electromagnetic radiation comprises means for emitting microwave radiation.

8. A system, comprising:
a processor; and
a plurality of electromagnetic radiation transmitters coupled to the processor, wherein each of the plurality of electromagnetic radiation transmitters are configured to emit electromagnetic radiation with a pseudorandom waveform,
wherein the processor is configured with processor-executable instructions to perform operations comprising configuring and controlling each of the plurality of electromagnetic radiation transmitters to emit electromagnetic radiation having a pseudorandom waveform configured so that the electromagnetic radiation constructively interferes within a volume for treatment and randomly interferes outside the volume for treatment of a subject.

9. A system, comprising:
a plurality of means for emitting electromagnetic radiation with a pseudorandom waveform; and
means for configuring and controlling each of the plurality of means for emitting electromagnetic radiation to emit electromagnetic radiation having a pseudorandom waveform configured so that the electromagnetic radiation constructively interferes within a volume for treatment and randomly interferes outside the volume for treatment of a subject.

* * * * *